United States Patent
Walters

(10) Patent No.: US 9,028,537 B2
(45) Date of Patent: May 12, 2015

(54) INFANT HEEL HEAT PACK

(71) Applicant: Dale E. Walters, Bonita Springs, FL (US)

(72) Inventor: Dale E. Walters, Bonita Springs, FL (US)

(*) Notice: Subject to any disclaimer, the term of this patent is extended or adjusted under 35 U.S.C. 154(b) by 0 days.

(21) Appl. No.: 13/754,315

(22) Filed: Jan. 30, 2013

(65) Prior Publication Data

US 2013/0144367 A1 Jun. 6, 2013

Related U.S. Application Data

(63) Continuation-in-part of application No. 13/273,610, filed on Oct. 14, 2011, now abandoned.

(60) Provisional application No. 61/451,242, filed on Mar. 10, 2011.

(51) Int. Cl.
| | |
|---|---|
| *A61F 7/00* | (2006.01) |
| *F24J 1/00* | (2006.01) |
| *F24J 3/00* | (2006.01) |
| *A61F 7/08* | (2006.01) |
| *A61F 7/03* | (2006.01) |
| *A61F 7/02* | (2006.01) |

(52) U.S. Cl.
CPC . *A61F 7/086* (2013.01); *A61F 7/03* (2013.01); *A61F 2007/0045* (2013.01); *A61F 2007/0095* (2013.01); *A61F 2007/0226* (2013.01); *A61F 2007/0244* (2013.01)

(58) Field of Classification Search
USPC .................. 607/96, 108–112, 114; 126/263.01–263.1, 204
See application file for complete search history.

(56) References Cited

U.S. PATENT DOCUMENTS

| | | | |
|---|---|---|---|
| 4,872,442 A | 10/1989 | Manker | |
| 5,058,563 A * | 10/1991 | Manker | 126/263.04 |
| 5,143,048 A | 9/1992 | Cheney, III | |
| 5,300,105 A * | 4/1994 | Owens | 607/114 |
| 5,305,733 A | 4/1994 | Walters | |
| 5,456,704 A * | 10/1995 | Kilcullen | 607/111 |
| RE35,586 E | 8/1997 | Manker | |
| 5,662,096 A * | 9/1997 | Walters | 126/263.03 |
| 5,791,334 A | 8/1998 | Walters | |
| 6,248,125 B1* | 6/2001 | Helming | 607/108 |
| 6,283,116 B1 | 9/2001 | Yang | |
| 6,878,157 B1 | 4/2005 | Walters | |
| 2005/0228466 A1* | 10/2005 | Harris | 607/114 |
| 2007/0067910 A1* | 3/2007 | Augustine et al. | 5/501 |
| 2008/0147153 A1* | 6/2008 | Quincy et al. | 607/114 |
| 2010/0078010 A1* | 4/2010 | Kolb | 126/263.08 |

\* cited by examiner

*Primary Examiner* — Joseph Stoklosa
*Assistant Examiner* — Adam Avigan
(74) *Attorney, Agent, or Firm* — Grace J. Fishel

(57) ABSTRACT

A heat pack for warming the heel of an infant with a front panel and a rear panel wherein the rear panel is adapted for placement on the infant's heel and has an outer layer formed of a nonwoven material which may be wetted. A band is provided for attaching the heat pack to the infant's heel. Heat from the heat pack effectively drives water applied to the nonwoven material into the infant's heel where it is then trapped in the skin under the heat pack. By thus moisturizing and softening the skin, a puncture necessary for taking a blood sample is eased.

9 Claims, 2 Drawing Sheets

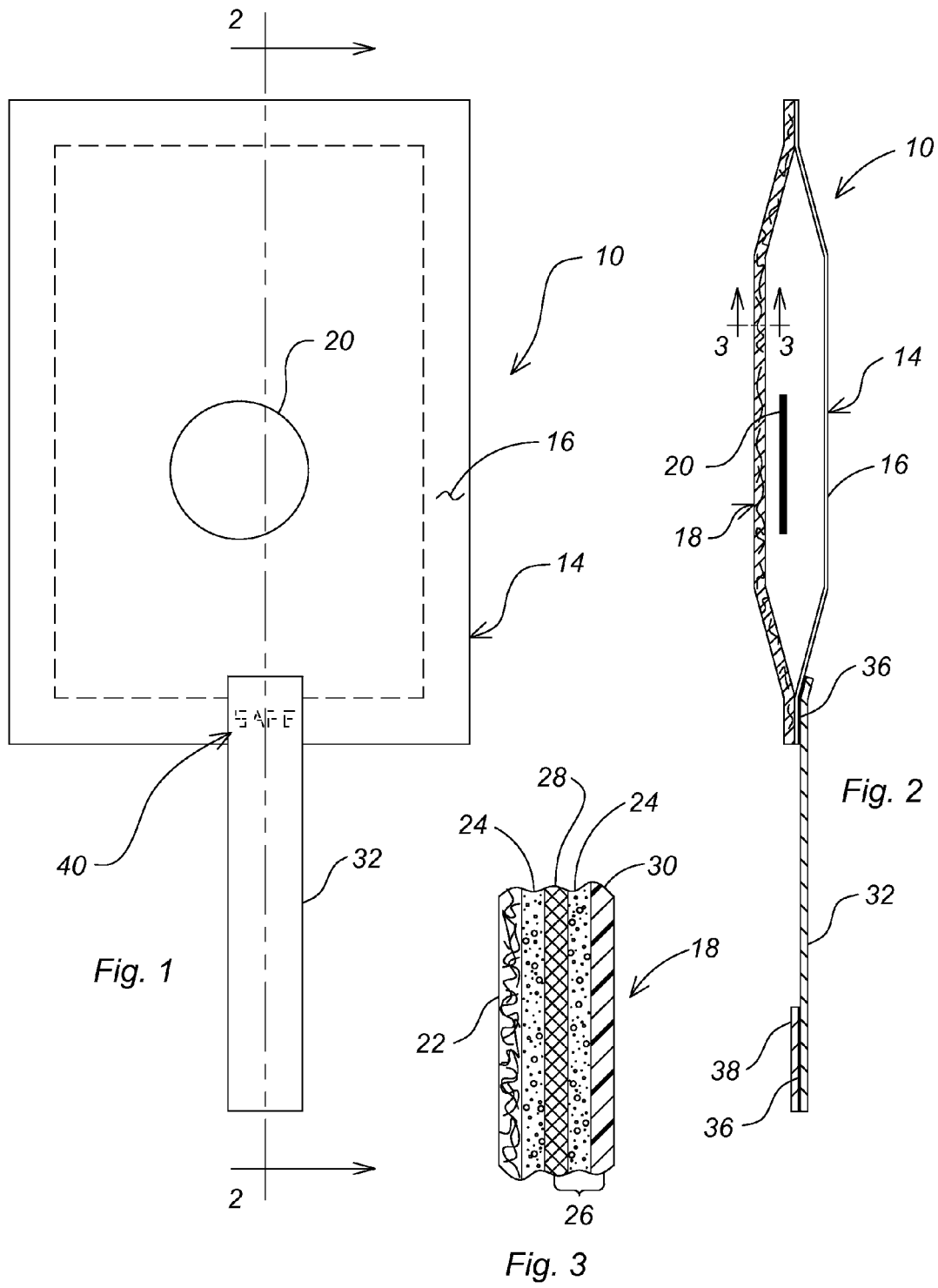

INFANT HEEL HEAT PACK

This application is a continuation-in-part of application Ser. No. 13/273,610, filed Oct. 14, 2011, which claims priority from provisional application Ser. No. 61/451,242, filed Mar. 10, 1011, for Infant Heel Heat Pack.

BACKGROUND OF THE INVENTION

1. Field of the Invention

The present invention relates to an infant heel heat pack with a nonwoven backing that is soft and skin friendly for contacting a baby's foot. The nonwoven backing insulates the infant's skin from burning, promotes the nesting of the heat pack around the heel and can be wetted to soften the skin.

2. Brief Description of the Prior Art

Blood samples are drawn from the heel of infants. To promote blood circulation in the heel area, heat is applied with a heat pack. Such heat packs are commonly formed as a plastic pouch with a supercooled aqueous salt solution. A trigger is included in the pouch which when manually manipulated initiates crystallization of the supercooled liquid releasing heat.

A front and back panel of a flexible polymer are sealed together about the side edges to form the plastic pouch which is preferably clear such that the trigger can be seen through the pouch. After crystallization has been triggered, the heat pack is taped on the infant's heel with the rear plastic panel pressed against the baby's skin. To soften the skin, nurses will wet the infant's heel with a wet cloth prior to inserting a needle.

BRIEF SUMMARY OF THE INVENTION

It is an object of the present invention to provide a user friendly heat pack for an infant's heel that moisturizes the skin to facilitate the necessary puncture to obtain a blood sample. It is another object to provide a heat pack that cuts back on potential irritation and nests around the heel during heating trapping water applied by the heat pack in the skin. Other objects and features of the invention will be in part apparent and in part pointed out hereinafter.

In accordance with the invention, a heat pack for warming the heel of an infant includes a plastic pouch with a front panel and a rear panel wherein the rear panel is adapted for placement on the heel of an infant and includes an outer layer formed of a nonwoven material capable of being wetted. Inside the pouch are a supercooled aqueous salt solution and a trigger capable of initiating crystallization.

The heat pack may have a band for attachment of the heat pack to the heel of an infant with a message formed with a thermochromic material that signals when the heat pack is at a temperature suitable for application to the heel of an infant. The band may also have a non-slip coating.

The invention summarized above comprises the constructions hereinafter described, the scope of the invention being indicated by the subjoined claims.

BRIEF DESCRIPTION OF THE SEVERAL VIEWS OF THE DRAWING

In the accompanying drawings, in which one of various possible embodiments of the invention is illustrated, corresponding reference characters refer to corresponding parts throughout the several views of the drawings in which:

FIG. 1 is a top plan view of a heat pack in accordance with the present invention;

FIG. 2 is a side, sectional view, taken along the plane of 2-2 in FIG. 1;

FIG. 3 is an enlarged sectional view, not to scale, taken along the plane of 3-3 in FIG. 2;

DETAILED DESCRIPTION OF THE INVENTION

Figure 4:
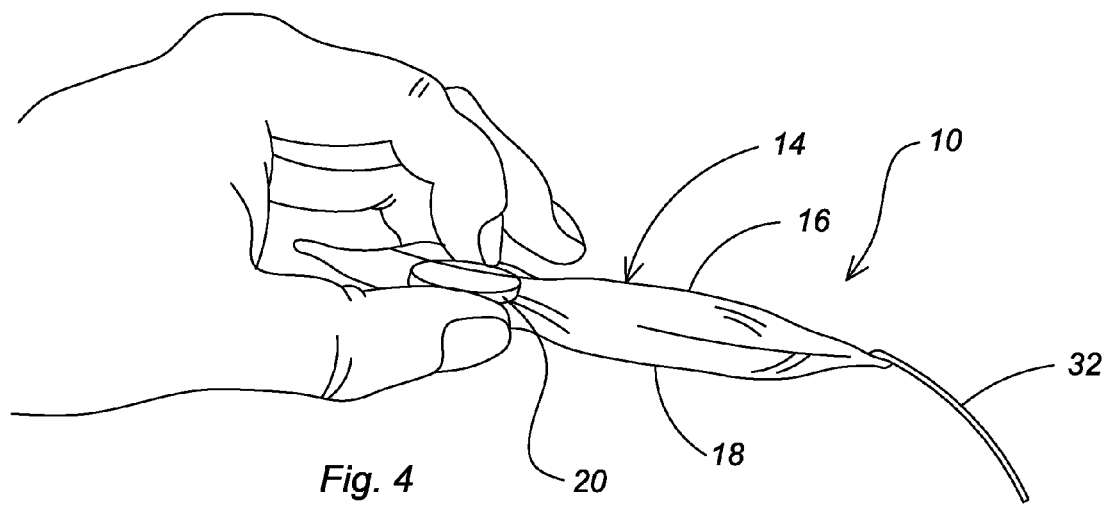
FIG. 4 is a side view of the heat pack showing manipulation of a trigger for initiating crystallization; and, FIG. 5 is a front elevation of an infant's foot showing the heat pack fastened on the infant's heel.

Referring to the drawings more particularly by reference number, reference numeral 10 refers to an infant heel heat pack in accordance with the present invention. An ideal but non-limiting size for heat pack 10 fitted to a baby's foot is 3½ by 5 inches. Heat pack 10 is formed as a flexible pouch 14 with a front panel 16 and a rear panel 18, the construction of which is discussed below.

Pouch 14 provides a container for a supercooled aqueous salt solution which, when activated releases heat. Suitable solutions include supercooled sodium acetate, lead acetate, calcium nitrate tetrahydrate, sodium pyrophosphate and sodium thiosulfate solutions. Sodium acetate may be preferred because it is generally harmless to humans.

The salt solution is made by dissolving the salt in a desired amount of water. The amount of salt to be utilized should permit the salt solution to be supercooled to at least the ambient temperature at which the heat pack is intended to be utilized. The supercooled aqueous salt solution may include a small amount of a viscosity increasing agent. A variety of gelling or thickening agents are commercially available, have been proposed for use in heat packs before and may be used.

As seen in FIGS. 1-2 and 4, a trigger 20 to initiate crystallization is included in pouch 14. Many triggers have been used in prior art heat packs and may be used in the present heat pack. For example, trigger 20 may be a metal disc or disc formed of flint, garnet, aluminum oxide, silicon carbide, alumina-zirconia, chromium oxide, ceramic aluminum oxide and so forth. What is important is that when trigger 20 is manually manipulated as shown in FIG. 4 by pressing the disc between thumb and index finger of one or both hands, the disc initiates crystallization.

Front panel 16 of pouch 14 can be made from a flexible plastic material. Suitable flexible materials include plastics used in the food industry such as polyolefins, copolymers of ethylene, substituted olefins, polyesters, polycarbonates, polyamides, acrylonitriles and so forth. A plastic laminate such as nylon polylaminate may also be used for front panel 16; suitable materials for such purpose having a thickness in the range of about 1 mil to 10 mils.

Rear panel 18 is formed as a laminate, an essential feature of which is that an outer layer 22 be formed of a nonwoven material. An illustrative cross-section of a rear panel 18 is shown in FIG. 3. Non-limiting examples of nonwoven materials suitable for outer layer 22 include nylon, rayon, cellulose ester, polyvinyl derivatives, polyolefins, polyamides, polyesters, natural materials such as wool, silk, jute, hemp, cotton, linen, sisal, ramie and combination thereof. The nonwoven material may be formed by a suitable process such as, for example melt blowing, spunbonding, card webbing, etc. For example, 42 gsm White SMS polypropylene untreated, Product Code B0116, sold by PGI of Mooresville, N.C. has been used. The polypropylene is spunbond and combined with meltblown polypropylene to form a layered SMS (spun-melt-spun) product. The polypropylene SMS is water-repellent but capable of adsorbing water on the surface and applying a film of water to an infant's heel. Other of the nonwoven materials mentioned above may also be wetted prior to application of the heat pack to an infant's heel.

An adhesive 24 attaches nonwoven outer layer 22 to an inner layer 26 which may be bonded to front panel 16. Inner layer 26 may also be a composite as shown in FIG. 3 wherein a first layer 28 is formed of a biaxial oriented polymer film. Biaxially oriented polyamides, polyethylene terephthalate or the like are generally much stronger in terms of tear strength and thus may be used to reinforce the nonwoven outer layer 22. A second layer 30 is formed of a flexible plastic material that can be bonded to or fused with the plastic material making up front panel 16. Front panel 16 and second layer 30 may be formed of the same material or not.

A specific example of rear panel 18 comprises nonwoven outer layer 22, adhesive 24, 60 gauge biaxially oriented nylon (BON) as first layer 28, adhesive 24 and 3 mil clear low linear density polyethylene (LLDPE) as second layer 30. The 60 gauge BON is manufactured by American Biaxis, Inc. Laminating adhesive 24 is sold under the trade name TYCEL and is manufactured by Henkel Adhesive. The LLDPE is manufactured by Appleton Performance Packaging-Films.

Figure 5:
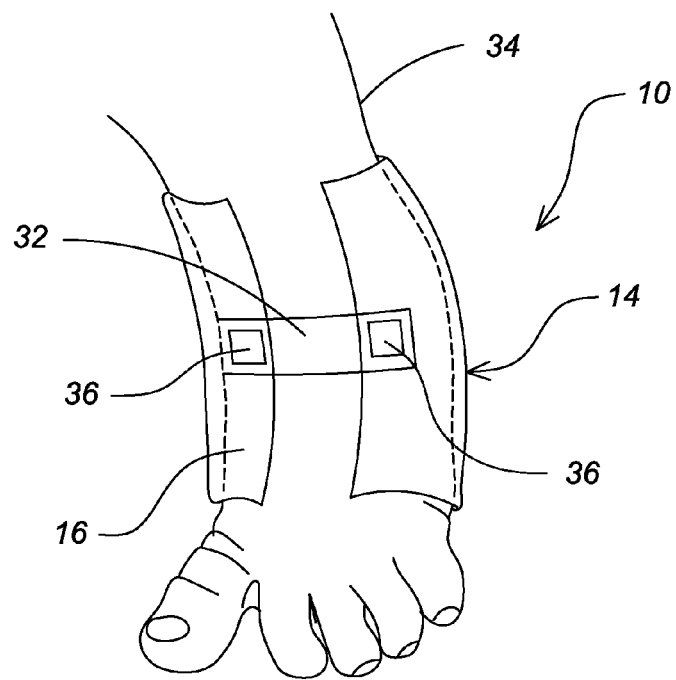

A band 32 is attached to heat pack 10 for the purpose of attaching the heat pack to a heel 34 of an infant as shown in FIG. 5. For this purpose a patch 36 of adhesive is provided on opposite ends of band 32 for connecting to front panel 16. Before heat pack 10 is applied to heel 34 and after crystallization has been initiated, a peel-off strip 38 over patch 36 as shown in FIG. 2 may be removed exposing patch 36 for attachment of the free end of band 32 to front panel 16. Band 32 may have a non-slip coating to keep heat pack 10 in place on an infant's heel.

A message 40 such as "Safe" as shown in FIG. 1, "Safe to Use" or the like may be printed on band 32 in a thermochromic ink or dye to let the operator know that heat pack 10 is at a proper temperature to be placed on infant's heel 34. For example, message 40 could appear when the temperature is somewhere between 98° and 105° Fahrenheit. Suitable thermochromic substances include liquid crystals and leucodyes. The indicator used for message 40 may include two or more different thermochromic materials that change color at different temperatures. For example, the indicator may include a first thermochromic material that is blue when heat pack 10 is below 98°, a second thermochromic material that turns green when heat pack 10 is within the desired temperature range, and a third thermochromic materials that turns orange when heat pack 10 is above 105°. Thermochromic materials can also be combined with non-thermochromic dyes and/or pigments to form message 40. For example, message 40 formed with non-thermochromic indicia may be obscured by a thermochromic coating that becomes translucent at a predetermined temperature, e.g., when a temperature above 105° has been reached.

In use, trigger 20 in heat pack 10 is flexed as shown in FIG. 4 initiating crystallization. When heat pack 10 has reached the suitable operating temperature, message 40 on band 32 may appear signaling that heat pack 10 is safe to apply to heel 34 of the infant and nonwoven outer layer 22 is preferably wetted. Strip 38 is peeled off patch 36 and heat pack 10 is attached to heel 34 with band 32 as shown in FIG. 5 with nonwoven outer layer 22 in contact with the baby's skin. As crystallization proceeds nonwoven layer outer layer 22 causes heat pack 10 to nest about the infant's heel thereby keeping it in place. Nonwoven outer layer 22 also insulates the infant's skin from burning and cuts back on potential irritation. The heat of the heat pack 10 drives water which has been applied to nonwoven outer layer 22 into the infant's skin where it is then trapped under the heat pack. The water moisturizes and softens the skin on the infant's heel thereby facilitating entry of a needle.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

What is claimed:

1. A heat pack for warming the heel of an infant comprising:
    a plastic pouch with a front panel and a rear panel wherein the rear panel is adapted for placement on the heel of an infant and includes an outer layer formed of a soft nonwoven and water repellant material formed of spun-melt-spun polypropylene and capable of applying a film of water to the heel of the infant,
    said front panel formed of plastic material,
    said outer layer of the rear panel formed of spun-melt-spun polypropylene wetted with a film of water and laminated to an inner layer formed of a biaxial oriented polymer film which is laminated to a plastic material that can be bonded or fused with the plastic material making up the front panel,
    a supercooled aqueous salt solution carried within said plastic pouch; and
    a trigger contained in the supercooled aqueous salt solution capable of initiating crystallization
    whereby the outer layer of soft nonwoven material formed of spun-melt-spun polypropylene permits nesting of the heat pack around the heel of an infant and is configured to apply the film of water and the biaxial oriented polymer film prevents tearing and slippage of the soft nonwoven material formed of spun-melt-spun polypropylene in use to which the biaxial oriented polymer film is laminated.

2. The heat pack of claim 1 having a band for attachment of the heat pack to the heel of an infant, said band having a message formed on the band with a thermochromic material that signals when the heat pack is at a temperature within the range of 98° and 105° F. and suitable for application to the heel of an infant.

3. The heat pack of claim 2 wherein the thermochromic material is a liquid crystal or leucodye.

4. The heat pack of claim 2 wherein the thermochromic material is a mixture of two or more different thermochromic materials that change color at different temperatures.

5. The heat pack of claim 4 wherein a first thermochromic material is a first color when the heat pack is below 98° F., a second thermochromic material is a second color when the heat pack is between 98° F. and 105° F. and a third thermochromic material is a third color when the heat pack is above 105° F.

6. The heat pack of claim 2 wherein the thermochromic material is a coating that becomes translucent at a predetermined temperature to reveal the message which is written with a non-thermochromic material.

7. The heat pack of claim 6 wherein the coating becomes translucent when the temperature is above 105° F.

8. The heat pack of claim 1 wherein the outer layer of nonwoven material is adhesively attached to the inner layer.

9. The heat pack of claim 1 wherein the biaxial oriented polymer film is 60 gauge biaxially oriented nylon and the flexible plastic material is low linear density polyethylene.

* * * * *